US012011605B2

United States Patent
Hussein

(10) Patent No.: US 12,011,605 B2
(45) Date of Patent: *Jun. 18, 2024

(54) FILTERED FEEDTHROUGH ASSEMBLY FOR USE IN IMPLANTABLE MEDICAL DEVICE AND METHOD OF MANUFACTURING THE SAME

(71) Applicant: Pacesetter, Inc., Sylmar, CA (US)

(72) Inventor: Haytham M. Hussein, Greer, SC (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/085,602

(22) Filed: Dec. 21, 2022

(65) Prior Publication Data

US 2023/0118734 A1 Apr. 20, 2023

Related U.S. Application Data

(63) Continuation of application No. 16/675,834, filed on Nov. 6, 2019, now Pat. No. 11,648,408.

(60) Provisional application No. 62/757,075, filed on Nov. 7, 2018.

(51) Int. Cl.
  *A61N 1/375* (2006.01)
  *A61N 1/37* (2006.01)
  *H01G 4/35* (2006.01)

(52) U.S. Cl.
  CPC ......... *A61N 1/3754* (2013.01); *A61N 1/3718* (2013.01); *A61N 1/37512* (2017.08); *H01G 4/35* (2013.01)

(58) Field of Classification Search
  CPC ........................... A61N 1/3718; A61N 1/3754
  See application file for complete search history.

(56) References Cited

U.S. PATENT DOCUMENTS

| | | | |
|---|---|---|---|
| 4,741,710 A | 5/1988 | Hogan et al. | |
| 5,333,095 A | 7/1994 | Stevenson et al. | |
| 6,888,715 B2 | 5/2005 | Stevenson et al. | |
| 7,038,900 B2 | 5/2006 | Stevenson et al. | |
| 10,596,369 B2 † | 3/2020 | Stevenson | |
| 10,874,865 B2 † | 12/2020 | Dollar | |

(Continued)

OTHER PUBLICATIONS

Document 1062 in *Greatbatch Ltd. v. AVX Corp. and AVX Filters Corp.*, D. Del. Civil Action No. 1:13-cv-723, Aug. 8, 2017 trial transcript, filed on ECF on Sep. 19, 2017, available at https://pacer.uscourts.gov/.†

*Primary Examiner* — Eugene T Wu
(74) *Attorney, Agent, or Firm* — Dean D. Small; The Small Patent Law Group

(57) ABSTRACT

A method of manufacturing a filtered feedthrough assembly for use with an implantable medical device. The method may include gold brazing an insulator to a flange at first braze joint, and gold brazing a plurality of feedthrough wire to the insulator at second braze joints. The method may further include applying a first non-conductive epoxy to the first braze joint, and applying a second non-conductive epoxy to the second braze joint. The method may further include grit blasting a face of the flange, applying a conductive epoxy to the face of the flange, and attaching an EMI filter to the conductive epoxy such that it is grounded to the flange via the conductive epoxy and not via the first braze joint or the second braze joints.

20 Claims, 14 Drawing Sheets

(56) References Cited

U.S. PATENT DOCUMENTS

| | | |
|---|---|---|
| 2002/0166618 A1 | 11/2002 | Wolf et al. |
| 2003/0179536 A1 | 9/2003 | Stevenson et al. |
| 2004/0257747 A1 | 12/2004 | Stevenson et al. |
| 2010/0134951 A1* | 6/2010 | Brendel ................. H01G 4/228 29/25.42 |
| 2013/0184797 A1 | 7/2013 | Tang et al. |
| 2019/0134407 A1* | 5/2019 | Dollar .................... H01G 4/224 |

\* cited by examiner
† cited by third party

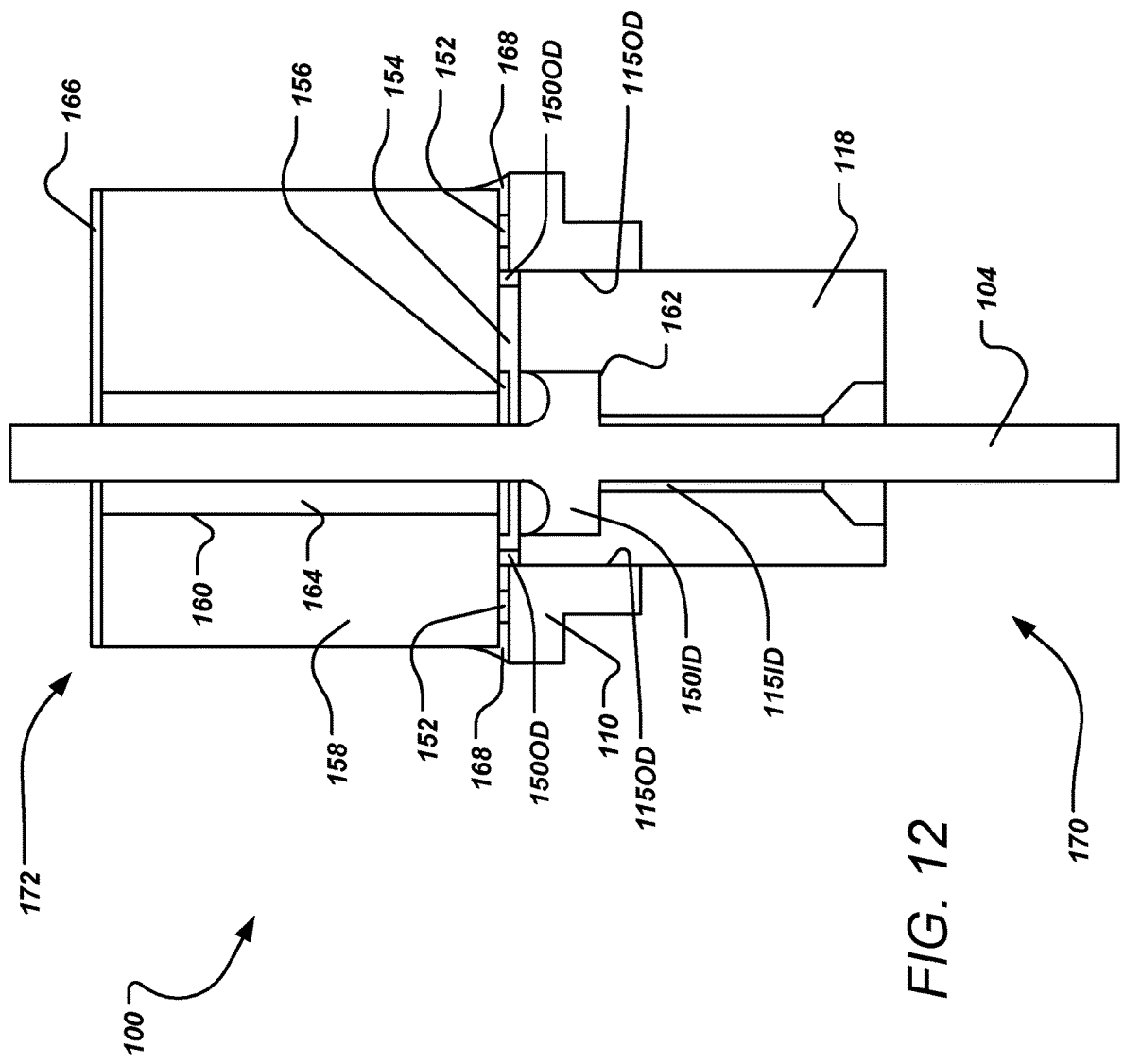

FILTERED FEEDTHROUGH ASSEMBLY FOR USE IN IMPLANTABLE MEDICAL DEVICE AND METHOD OF MANUFACTURING THE SAME

CROSS-REFERENCE TO RELATED APPLICATIONS

The present application is a continuation application of, and claims priority to, U.S. application Ser. No. 16/675,834, which was filed on 6 Nov. 2019, which claims priority to U.S. Application No. 62/757,075, filed 7 Nov. 2018, the complete subject matter of which are expressly incorporated herein by reference in their entirety.

FIELD OF THE INVENTION

The present disclosure is directed to feedthrough filter assemblies for use in implantable medical devices such as, for example, cardiac rhythm management and pacemaker devices. More specifically, the present disclosure is directed to the attachment and grounding of capacitors in feedthrough filter assemblies.

BACKGROUND OF THE INVENTION

Implantable pulse generators, including cardiovascular implantable electronic devices ("CIED") such as pacemakers and implantable cardioverter defibrillators ("ICD"), are used to provide therapy to cardiac tissue, nerves and other tissue via implantable leads. An implantable pulse generator feedthrough or feedthru is used for an electrical pathway extending between the electrically conductive lead securing components of a header of the pulse generator and the electrical components, such as an output flex, hybrid, etc., hermetically sealed in the housing or can of the pulse generator.

Feedthroughs provide insulated passageways for feedthrough wires, such as palladium/iridium (Pd/Ir) wires, through the wall of the can. The header ends of the feedthrough wires are electrically connected to connector blocks that mechanically and electrically couple with proximal connector ends of implantable leads, and the can ends of the feedthrough wires are electrically connected to the electrical components housed in the can of the pulse generator such as the Hybrid Board.

Implantable pulse generators may include electromagnetic interference ("EMI") filters for filtering out unwanted EMI signals interfering with the signals from the lead wires. Conventionally, the EMI filter is a capacitor that is sandwiched between the feedthrough and the board. The capacitors are built as monolithic structures that are internally grounded to a flange of the feedthrough assembly. Past attempts at grounding the capacitor to the flange relied on the gold within the braze joint between the insulator and flange to also contact the capacitor and thus provide a conductive path for grounding. This type of grounding can be highly variable depending on the quality of the brazing and the gold mixture within the braze joint. For example, a very thin gold strip between the insulator and the flange may provide excessive resistivity, making the ground unusable in the context of implantable pulse generators. Other problems of relying on the braze material for grounding purposes include the potential for braze failures, for example caused by mechanical strain on the feedthrough assembly and thermal stressing of the braze material.

Accordingly, there is a need in the art for filtered feedthrough assemblies and implantable pulse generators with filtered feedthrough assemblies that are internally grounded that do not rely on grounding through braze material so that improved reliability of the implantable pulse generator is achieved when exposed to interferences, such as Electrical Magnetic Interference.

SUMMARY OF THE INVENTION

Aspects of the present disclosure may include a filtered feedthrough assembly for an implantable pulse generator. The filtered feedthrough assembly may include: a flange; a plurality of feedthrough wires, a ceramic insulator; an EMI filter; a first non-conductive washer; first and second non-conductive epoxies; and an electrically conductive material. The flange is made of an electrically conductive material and includes a can side, a header side, a can side face, and a feedthrough port having an inner surface and extending through the flange from the can side to the header side. The plurality of feedthrough wires may extend through the feedthrough port. The ceramic insulator may include an outer surface and a plurality of ports extending there through, each of the plurality of ports including a counter bore, the outer surface of the ceramic insulator gold brazed to the inner surface of the first feedthrough port of the flange at a first braze joint. The plurality of feedthrough wires respectively extend through and are gold brazed to the first plurality of ports of the first ceramic insulator at second braze joints. The EMI filter may include a capacitor having a plurality of ports extending there through. The plurality of feedthrough wires respectively extend through the plurality of ports of the capacitor. The first non-conductive washer may be positioned between the ceramic insulator and the capacitor. The first non-conductive epoxy may cover the first braze joint around a periphery of the outer surface of the ceramic insulator so as to insulate the first braze joint from the capacitor. The second non-conductive epoxy may be positioned within the counter bores of the plurality of ports of the ceramic insulator so as to insulate the second braze joint from the capacitor. And the electrically conductive material may couple and provide a ground from the capacitor to the flange.

In certain instances, the electrically conductive material includes silver epoxy.

In certain instances, the electrically conductive material is coupled to the can side face of the flange.

In certain instances, the electrically conductive material is coupled to the can side face in two strands adjacent long edges of the feedthrough port of the flange.

In certain instances, the can side face includes a sand blasted surface coupled to the electrically conductive material.

In certain instances, the filtered feedthrough assembly may further include a polyimide film disc washer positioned between the first non-conductive washer and the capacitor. In certain instances, the polyimide film disc washer is made of Kapton.

In certain instances, the filtered feedthrough assembly may further include a second non-conductive washer positioned on the capacitor opposite the first non-conductive washer.

In certain instances, the filtered feedthrough assembly may further include a conductive silver epoxy bonding the plurality of feedthrough wires and the plurality of ports of the capacitor.

Aspects of the present disclosure may include an implantable pulse generator including: a header; a can; and a filtered feedthrough assembly. The header may include lead connector blocks. The can may be coupled to the header and include a wall and an electronic substrate housed within the wall. The filtered feedthrough assembly may include a flange mounted to the wall of the can and having a feedthrough port, a plurality of feedthrough wires extending through the feedthrough port and electrically connecting the lead connector blocks and the electronic substrate, an insulator brazed to the feedthrough port of the flange at a first braze joint and brazed to the plurality of feedthrough wires at second braze joints, a capacitor having the plurality of feedthrough wires extending there through, a first non-conductive epoxy insulating the first braze joint from electrical connection with the capacitor, a second non-conductive epoxy insulating the second braze joints from electric connection with the capacitor, and an electrically conductive material adhered to the capacitor and the flange for grounding of the capacitor.

In certain instances, the filtered feedthrough assembly may further include a non-conductive washer positioned between the insulator and the capacitor.

In certain instances, the filtered feedthrough assembly may further include a polyimide film disc washer positioned between the non-conductive washer and the capacitor. In certain instances, the non-conductive washer includes an electrically non-conductive double-sided adhesive.

In certain instances, the electrically conductive material couples to a portion of a face of the flange.

In certain instances, the portion of the face of the flange is a soda blasted portion of the flange.

In certain instances, the electrically conductive material includes a conductive silver epoxy.

Aspects of the present disclosure may include a method of manufacturing a filtered feedthrough assembly for use with an implantable medical device. The method may include gold brazing an insulator to a flange at first braze joint. The method may additionally include gold brazing a plurality of feedthrough wire to the insulator at second braze joints. The method may additionally include applying a first non-conductive epoxy to the first braze joint. The method may additionally include applying a second non-conductive epoxy to the second braze joint. The method may additionally include grit blasting a face of the flange, applying a conductive epoxy to the face of the flange, and attaching an EMI filter to the conductive epoxy such that it is grounded to the flange via the conductive epoxy and not via the first braze joint or the second braze joints.

In certain instances, the method may further include attaching a non-conductive washer between the insulator and the EMI filter.

In certain instances, the method may further include positioning a polyimide film disc washer between the non-conductive washer and the EMI filter.

In certain instances, the method may further include electrically coupling the EMI filter and the plurality of feedthrough wires using conductive silver epoxy.

BRIEF DESCRIPTION OF THE DRAWINGS

FIG. 12 is a cross-sectional side view of a filtered feedthrough assembly taken along the section line from FIG. 8.

DETAILED DESCRIPTION

The present disclosure describes a filtered feedthrough assembly of an implantable pulse generator such as, for example, a pacemaker or an ICD. For a general discussion of an implantable pulse generator 5 that utilizes a feedthrough assembly coupled to a filter (e.g., capacitor) and an inline array feedthrough board, reference is first made to FIG. 1.

Figure 1:
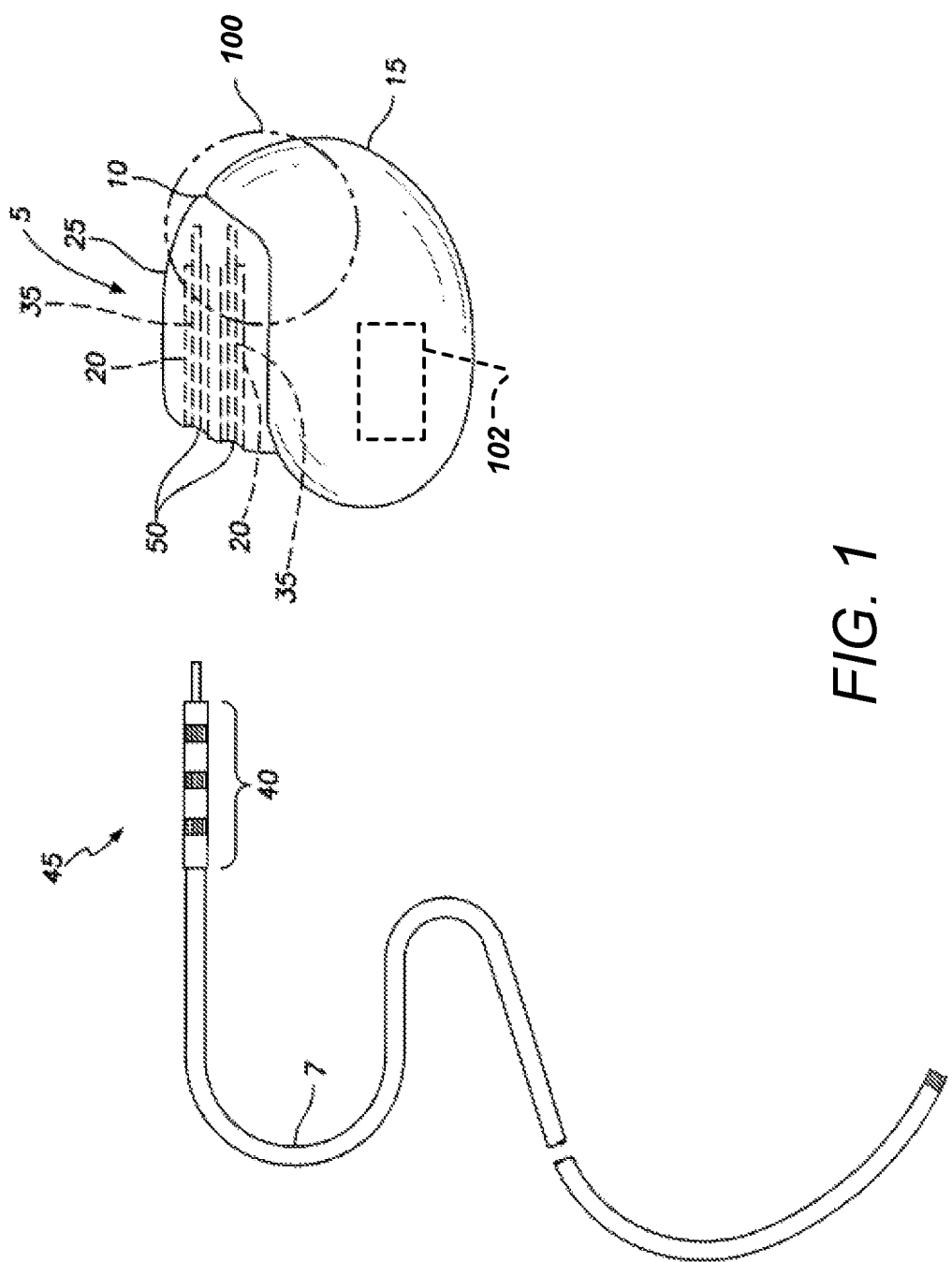
FIG. 1 is a side view of a pulse generator and an implantable lead positioned to be coupled to the pulse generator.

FIG. 1 is a side view of a pulse generator 5 and an implantable lead 7 positioned to be coupled to the pulse generator. As indicated in FIG. 1, the pulse generator 5 includes a header 10 and a can or housing 15. The header 10 includes connector blocks 20 and a molded portion 25 that encloses the connector blocks 20. Each connector block 20 includes an opening 35 configured to receive therein and mate with a connector end 40 of a proximal end 45 of an implantable lead 7, thereby forming an electrical connection between the connector block 20 and the lead connector end 40 and mechanically securing the proximal end 45 of the lead 7 to the header 10 of the pulse generator 5.

The molded header portion 25 may be formed of a polymer material or epoxy. Passages 50 extend from the exterior of the molded portion 25 to the openings 35 in the connector blocks 20 provide a pathway for the lead distal ends 40 to pass through the molded portion 25 and enter the openings 35.

The feedthrough assembly 100, generally located by the broken line circle in FIG. 1, provides an electrical connection between the fixed electrical components 102 within the can 15 and the releasable connection with the connector ends 40 of the proximal end 45 of the lead 7. The can 15 provides a hermetically sealed enclosure for the pulse generator's electronic components (e.g., hybrid, or various other electronic components), which are mounted on, and electrically interconnected via, an electronic substrate, all of which are housed within the can 15. As described previously, the feedthrough assembly 100 may be a filtered feedthrough assembly 100 with the addition of a filtering component, such as an EMI filter. And while an EMI filter is referenced herein, the filtering component may be other types of filters without limitation.

Figure 2A:
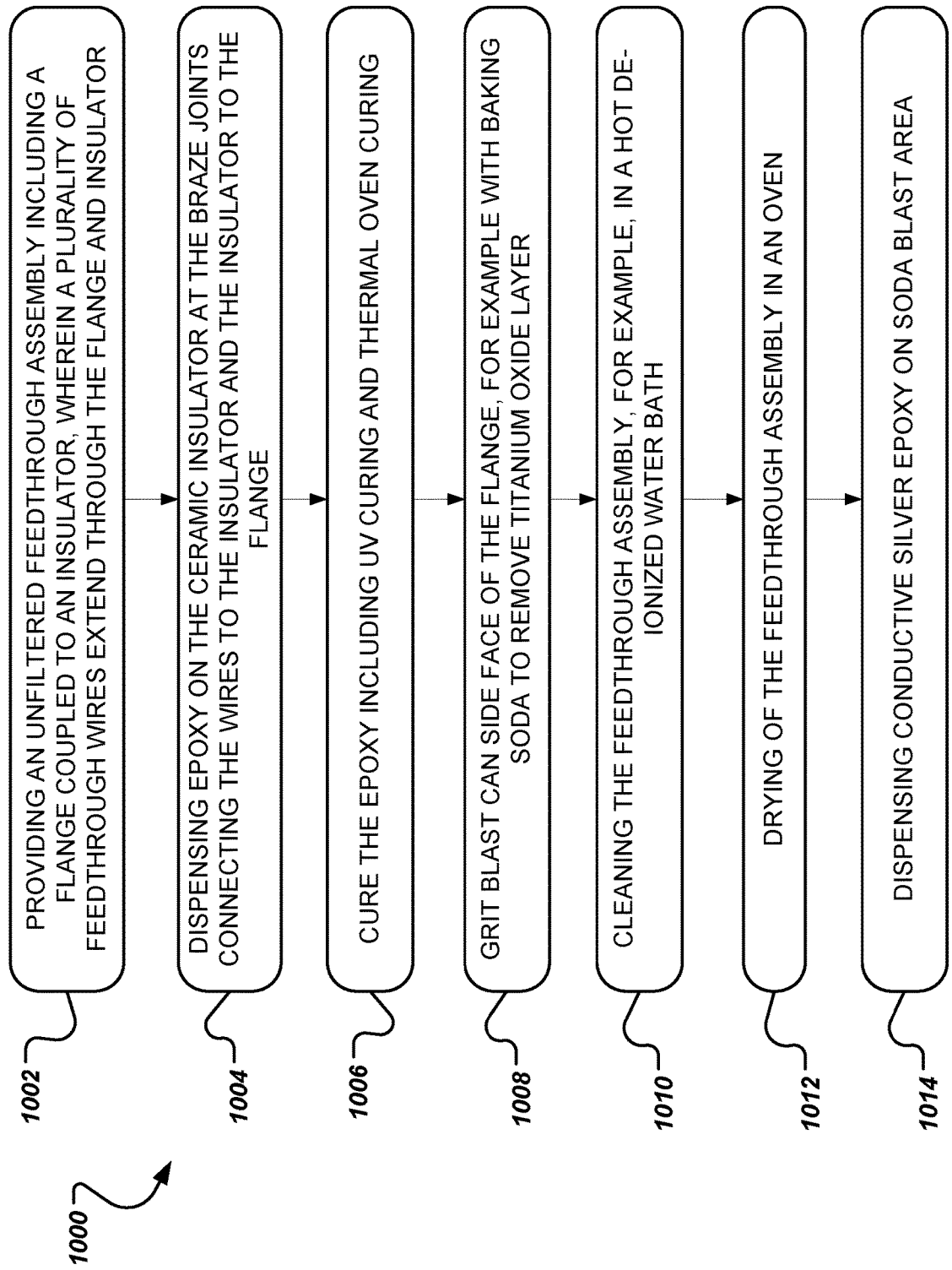
FIGS. 2A-2C show a flowchart of exemplary steps in a method of producing the filtered feedthrough assembly.

To begin the discussion of the filtered feedthrough assembly 100, reference is made to FIG. 2A, which is a flowchart of exemplary steps of a method 1000 of manufacturing the filtered feedthrough assembly 100. At step 1002, the method 1000 includes providing an unfiltered feedthrough assembly 100 including a flange 110 and an insulator 118, with a series of feedthrough wires 104 extending through the assembly 100.

Figure 3:
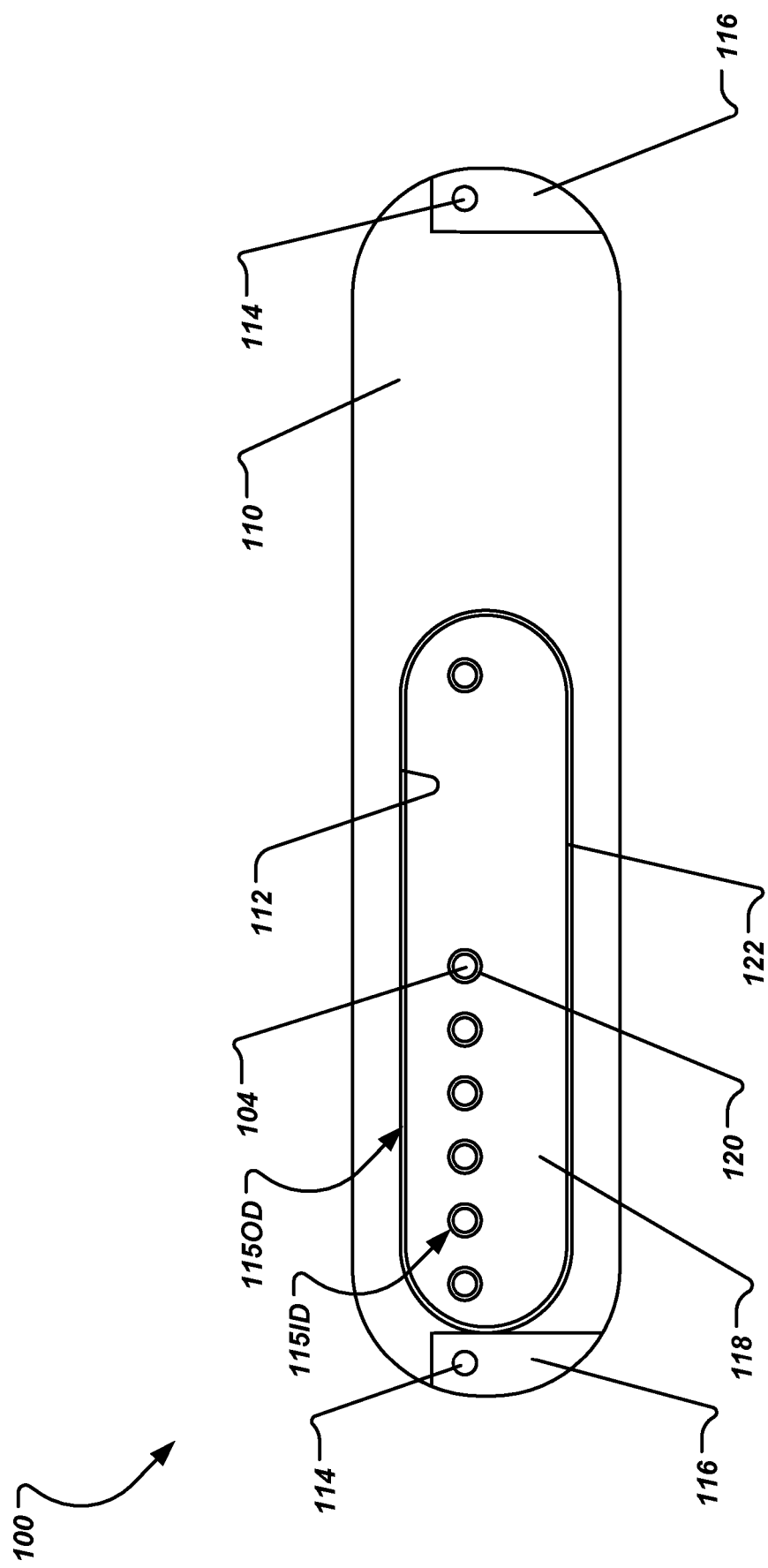
FIG. 3 is a top or can side view of a flange and an insulator coupled together in a process of manufacturing a filtered feedthrough assembly.

To illustrate the filtered feedthrough assembly at step 1002, reference is made to FIG. 3, which depicts a top or can side view of a flange 110 and insulator 118 in the midst of a manufacturing process to become a filtered feedthrough assembly 100. As described herein, the can side is the side of the filtered feedthrough assembly 100 that leads to the can, as opposed to a header side of the assembly. The feedthrough assembly 100 includes feedthrough wires 104 that extend from the can side to the header side of the assembly 100. The feedthrough wires 104 may be made of gold, palladium, platinum, nickel, titanium, MP35N, niobium, or any other suitable conductive material.

The flange 110 of the filtered feedthrough assembly 100 includes an elongated body and a feedthrough port 112 through which the feedthrough wires 104 extend. While the present disclosure describes a single feedthrough port 112, the description herein is applicable to a feedthrough assembly 100 having additional feedthrough ports 112, for example two feedthrough ports 112. As seen in the figure, the port 112 is an elongated rectangular port having rounded ends that extend through the flange 110 from the can side to the header side. And as seen in FIG. 3, seven feedthrough wires 104 extend through the feedthrough port 112 of the flange 110 and the insulator 118.

The filtered feedthrough assembly 100 includes two ground pins 114 that may be electrically connected with the internal electronics 102 (not seen in FIG. 3) on the inside of the can 15 (not seen in FIG. 3). As seen in FIG. 3, each of the ground pins 114 may terminate at a projection 116 that juts out from the elongated body of the flange 110. The flange 110 is formed of an electrically conductive material, and therefore provides a conductive path between the ground pins and the can 15 within which the flange 110 is disposed.

The feedthrough wires 104 are isolated from contact with each other and the flange 110 by a ceramic insulator 118 that is sized to fit within the feedthrough port 112 of the flange 110. The ceramic insulator 118 (generally referred to as an insulator) is formed of a non-conducting material and includes a series of wire ports 120 for the feedthrough wires 104 to extend through. The ceramic insulator 118 includes an outer surface 122 sized just smaller than the feedthrough port 112. In this instance, the ceramic insulator 118 includes seven wire ports 120 to accommodate the seven feedthrough wires 104.

To couple the flange 110 and the insulator 118, the outer surface 122 of the ceramic insulator 118 is brazed to the inner surface of the feedthrough port 112 of the flange 110 at a braze joint 115OD using gold, nickel, platinum, or other suitable material as the braze material. This braze joint 115OD may be referred to as "OD gold", meaning the outer diameter of the insulator 118 is gold brazed to the flange 110. As an alternative to brazing, the ceramic insulator 118 may be coupled to the flange via soldering, welding, or other suitable methods. The feedthrough wires 104 may also be connected to the ports 120 of the ceramic insulators 118 via brazing at a braze joint 115ID, which may be referred to as "ID gold", meaning the inner diameter of the ports 120 are gold brazed to the wires 104. Alternatives to brazing may include soldering, welding, or other suitable joining methods. These methods help ensure a hermetic seal through the filtered feedthrough assembly 100.

Figure 4:
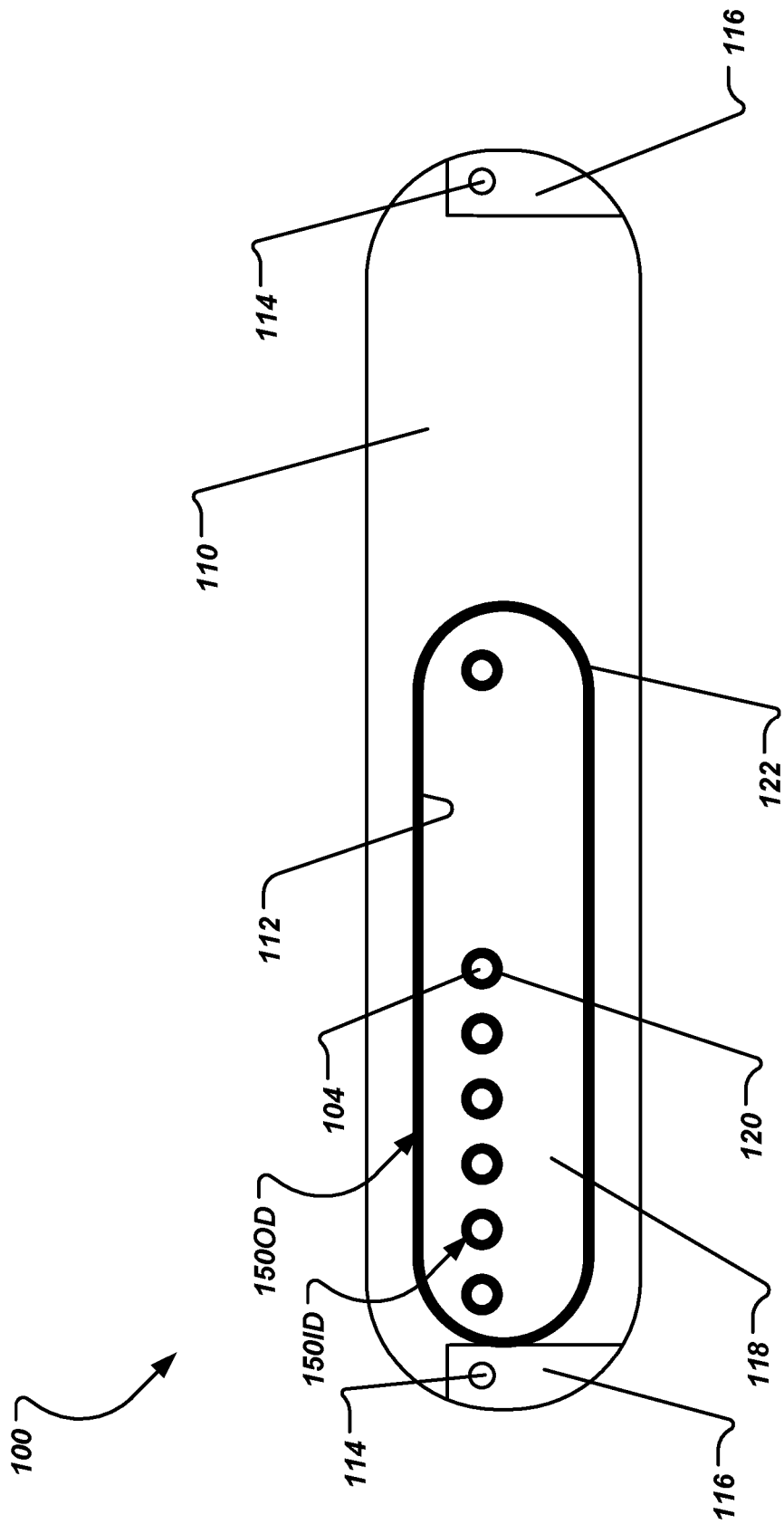
FIG. 4 is a top side view of the flange and the insulator coupled together with epoxy adhered to the gold braze areas.

Referring back to FIG. 2A, step 1004 of the method 1000 may include dispensing epoxy 150OD, 150ID on the ceramic insulator 118 of the feedthrough assembly 110 at the braze joints 115OD, 115ID, as illustrated in FIG. 4. FIG. 4 depicts a can side view of the filtered feedthrough assembly 100 with a coat of epoxy 150ID, 150OD over the braze joints 115ID, 115OD. As an example, the epoxy 150ID, 150OD may be a UV curable epoxy. UV curable epoxies do not require the addition of curing agents, and begin to cure with the application of UV light. As seen in FIG. 4, the epoxy 150ID, 150OD covers all gold braze material on the feedthrough assembly 100, including the gold braze 115ID coupling the feedthrough wires 104 and the feedthrough ports 120 of the ceramic insulator 118, and the gold braze 115OD coupling the outer surface 122 of the ceramic insulator and the inner surface of the port 112 of the flange 110. In this way, an EMI filter that is coupled to the flange 110 will not contact the gold braze joints 115ID, 115OD. And therefore, the gold braze joints 115ID, 115OD will not ground the EMI filter and the gold joint 115ID will not contact the silver epoxy 160 illustrated in FIG. 9 and described with reference to step 1028 of the method 1000 of FIG. 2B. This avoids the pitfalls of relying on such a connection as described in the Background section of this application.

Continuing on, step 1006 of the method 1000 of FIG. 2A may include curing the epoxy 150ID, 150OD. This may include curing the epoxy 150ID, 150OD with ultraviolet light, followed by a thermal oven cure of the epoxy 150ID, 150OD. Next, step 1008 of the method 1000 of FIG. 2A may include grit blasting at least a portion of the can side face of the flange 110 (up to and including substantially all of the can side face of the flange 110), for example, with baking soda to remove an oxide layer (e.g., a titanium oxide layer when the flange 110 is formed from titanium) so as to reduce surface oxidation. Other methods for removing oxide may be performed without limitation. For example, plasma etching and/or acid etching may be utilized to remove oxide. The parts may then be placed in a parts fixture and ultrasonically cleaned in a hot de-ionized water bath (which, in certain implementations and without limitation, may be approximately 85 degrees Celsius), at step 1010. The feedthrough filter 100 may then be dried in an oven, at step 1012.

Figure 5:
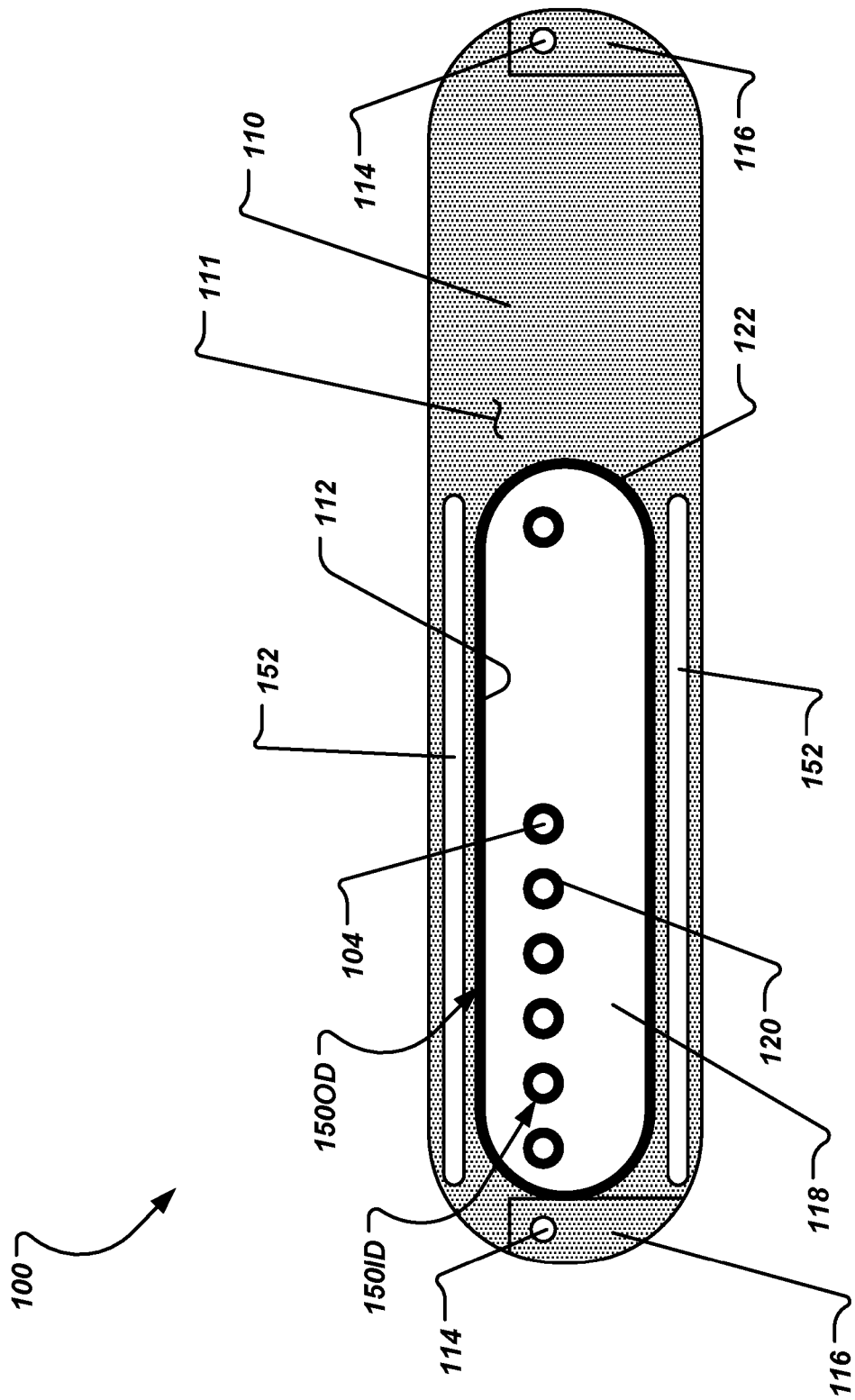
FIG. 5 is a top side view of the flange and the insulator where the flange is soda blasted and two beads of conductive adhesive are applied to the face of the flange.

Next, at step 1014, the method 1000 of FIG. 2A may include dispensing conductive silver epoxy 152 on the soda blasted face 111 of the flange 110. FIG. 5 depicts the can side of the feedthrough assembly 100 with silver epoxy 152 dispensed or applied to the face 111 of the flange 110. As shown in FIG. 5, in at least some implementations, the silver epoxy 152 may be dispensed as single continuous strands; however, in other implementations, the silver epoxy 152 may be dispensed as multiple strands or beads. The strands of silver epoxy 152 are positioned between the long edges of the feedthrough ports 112 of the flange 110 and the top and bottom edges of the flange 110. As seen in FIG. 5, the entire face 111 of the can side of the flange 110 appears textured from the soda blasting to remove the titanium oxide layer.

Figure 2B:
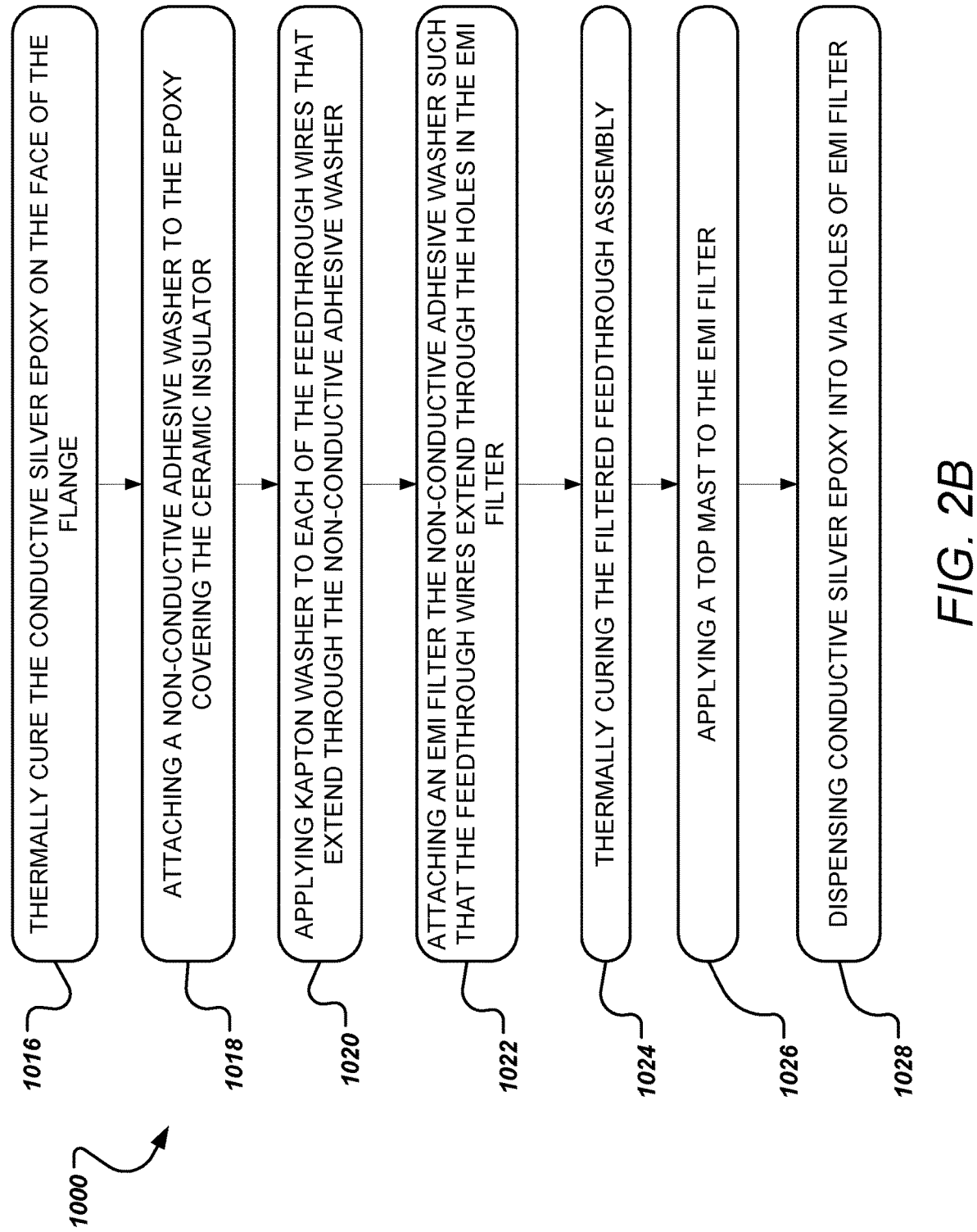
Figure 6:
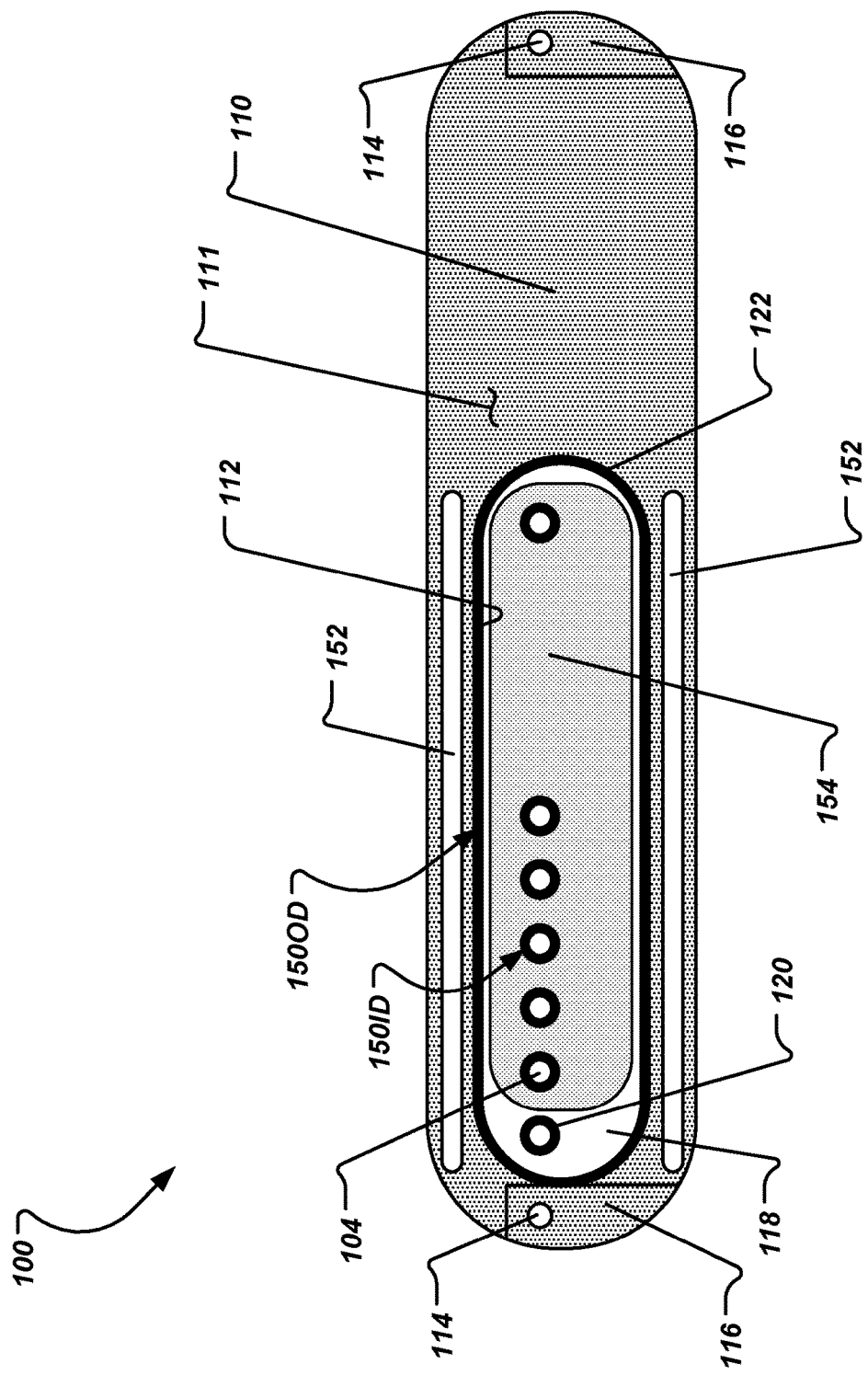
FIG. 6 is a top side view of the flange and the insulator of FIG. 5 with a non-conductive adhesive washer applied to the insulator.

After applying the conductive silver epoxy 152 on the face of the flange 110, the feedthrough assembly 100 may be placed in an oven to thermally cure the conductive silver epoxy 152. This step 1016 of the method 1000 is shown in FIG. 2B. Next, step 1018 of the method 1000 in FIG. 2B, includes attaching a non-conductive adhesive washer 154 to the ceramic insulator 118. FIG. 6 illustrates the non-conductive adhesive washer 154 including a plurality of through-holes that are sized and spaced-apart to fit over the feedthrough wires 104. The shape of the non-conductive adhesive washer 154 also substantially matches that of the ceramic insulator 118, except that the ceramic insulator may be longer. As seen in FIG. 6, one or more of the feedthrough wires 104 may not extend through the non-conductive adhesive washer 154.

Figure 7:
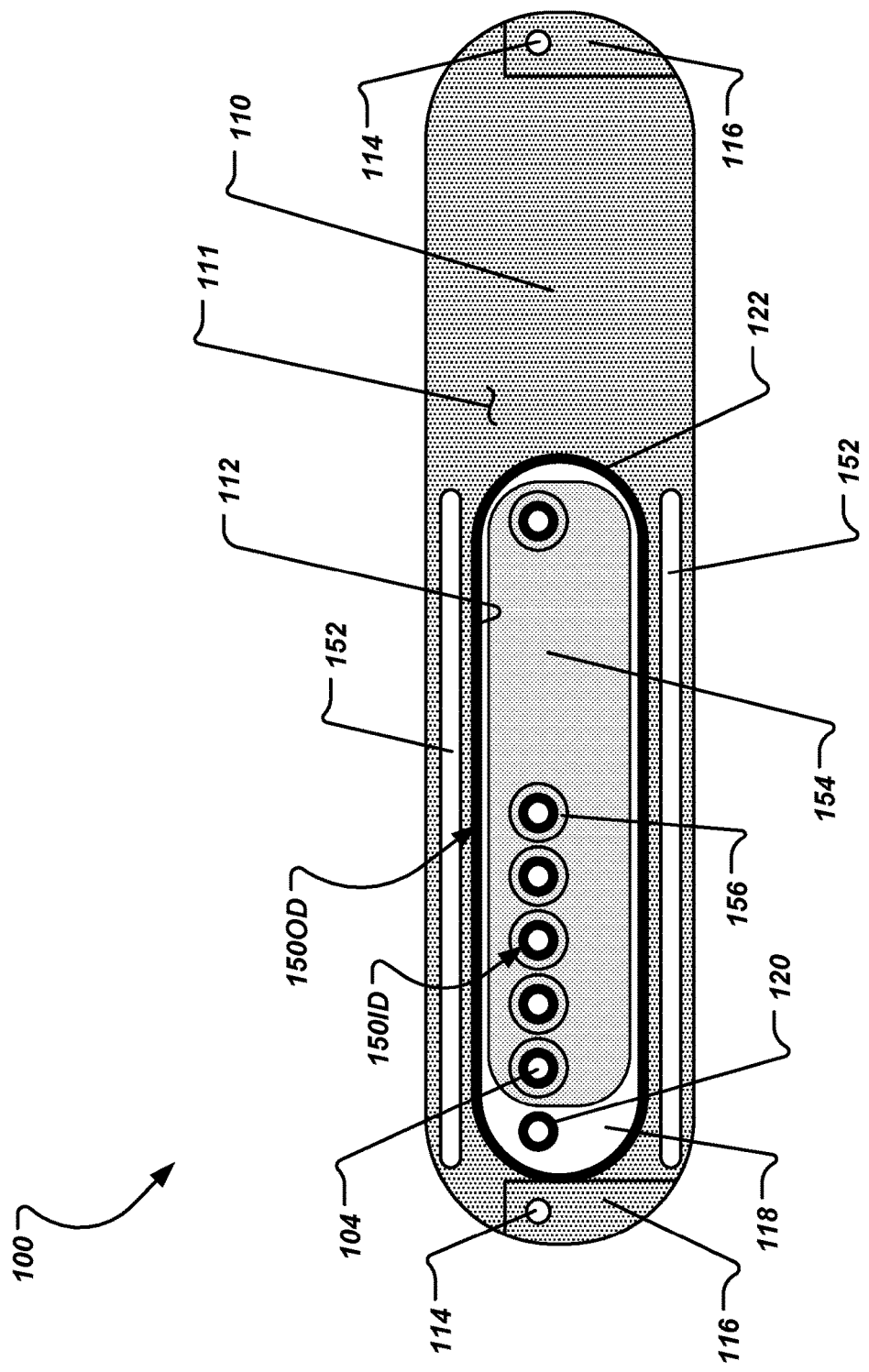
FIG. 7 is a top side view of the flange, insulator, and non-conductive washer of FIG. 6 with washers applied to the non-conductive adhesive washer over the wires.

Once the non-conductive adhesive washer 154 is attached to the epoxy 150, individual washers 156 are applied to the feedthrough wires 104 that extend through the non-conductive adhesive washer 154, at step 1020 of FIG. 2B. In certain implementations, the washers 156 may be formed from Kapton® or a similar insulative or non-conductive material. The washers 156 are placed on top of the non-conductive adhesive washer 154, as seen in FIG. 7.

Figure 8:
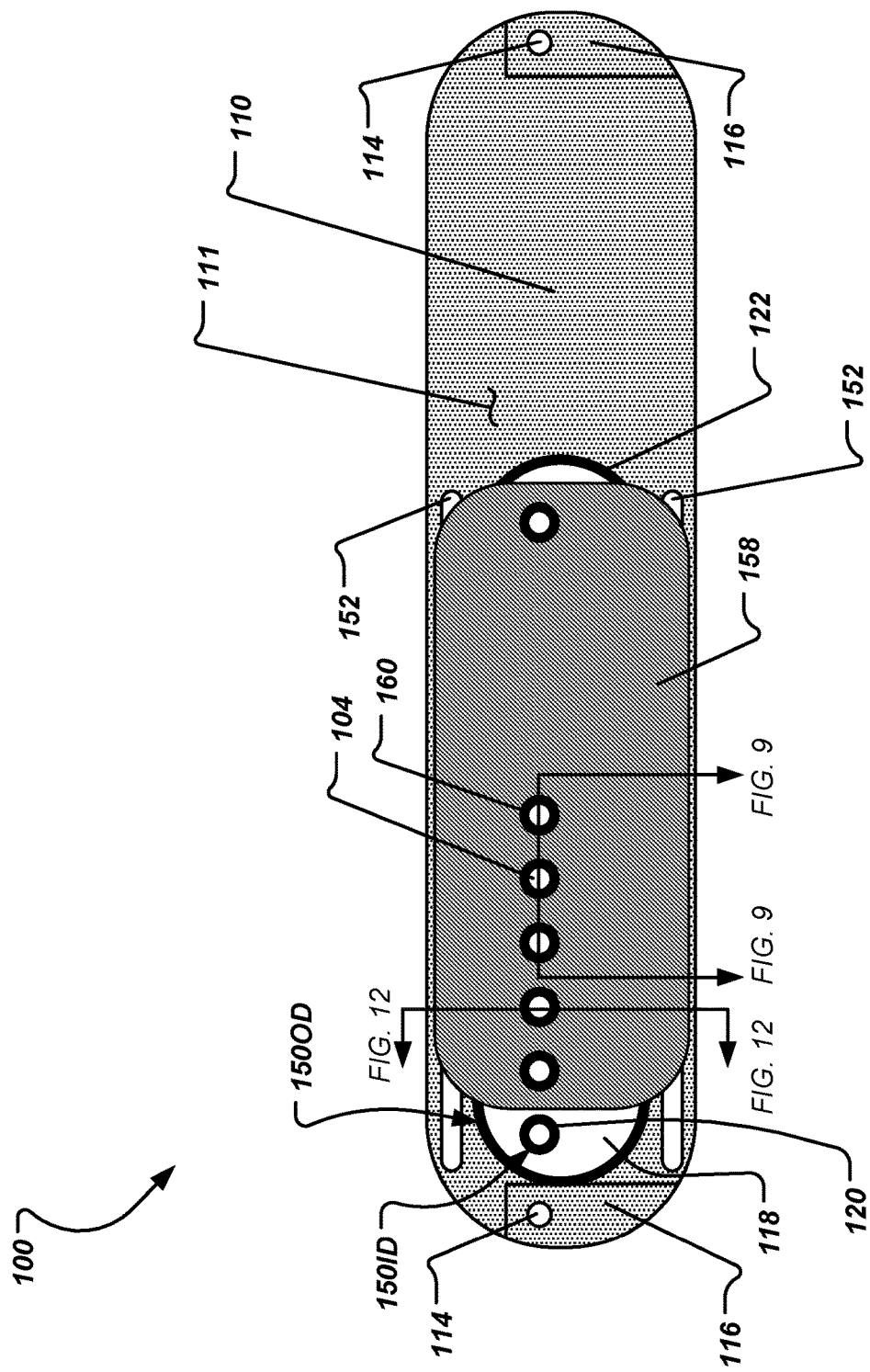
FIG. 8 is a top side view of an EMI filter attached to the assembly of FIG. 7.

Next, step 1022 of the method 1000 of FIG. 2B includes attaching an EMI filter (e.g., capacitor) 158 having a plurality of through-holes 160 to the non-conductive adhesive washer 154 by receiving the feedthrough wires 104 of the feedthrough assembly 100 within the plurality of through-holes 160 of the EMI filter 158. FIG. 8 shows the EMI filter 158 attached to the flange 110 via the conductive silver epoxy 152 on the face 111 of the flange 110. The EMI filter 158 must be grounded in order to function properly. As seen in FIG. 8, the EMI filter 158 is electrically coupled to the flange 110 via the conductive silver epoxy 152. In this way, the EMI filter 158 is grounded by the conductive silver epoxy 152 and avoids all potentially variable contact areas associated with the gold brazing that is insulated via the non-conducting epoxy 150ID, 150OD.

Additional conductive silver epoxy 168 may be applied to the face 111 of the flange 110 adjacent the conductive silver epoxy 152, as seen in FIG. 12. The conductive silver epoxy 168 may extend onto one or both of the side surfaces of the EMI filter 158 and the flange 110 so as to increase the surface area for grounding of the EMI filter 158 to the flange 110. In the case of a flange 110 that is wider than the EMI filter 158, as seen in FIG. 12, the joint between the two components may be filled with the conductive silver epoxy 168 to form a radiused, smooth joint surface. Utilizing the opposing surfaces between the EMI filter 158 and the flange 110 in addition to the side surfaces of the EMI filter 158 and the flange 110 can greatly increase the surface area for grounding as compared to the former methods of relying on the braze joint between the insulator and flange to also contact the capacitor and thus provide a conductive path for grounding. In certain instances, the addition of the conductive silver epoxy 168 may be disregarded in favor of utilizing the previously applied conductive silver epoxy 152 described previously.

Figure 9:
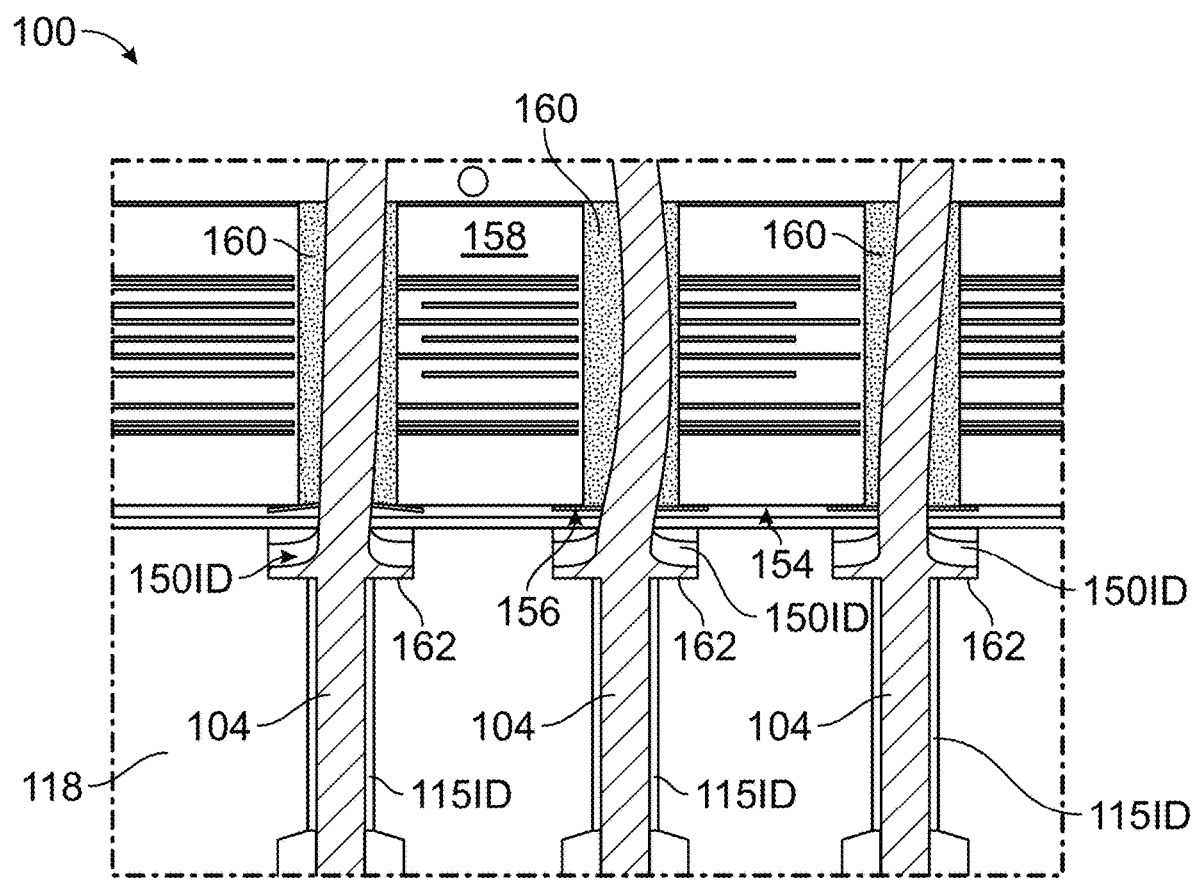
FIG. 9 is a cross-sectional side view of three feedthrough wires and a portion of the EMI filter and the insulator taken along the section line from FIG. 8.

FIG. 9 illustrates a cross-sectional view of the filtered feedthrough assembly 100 along the cross-sectional line indicated in FIG. 8. In particular, FIG. 9 shows three feedthrough wires 104 extending through the EMI filter 158 and the ceramic insulator 118. As seen in the figure, the UV curable epoxy 150ID is located in the counter bore 162 of the insulator 118. Just above the insulator 118 is the non-conductive adhesive washer 154, and then the washers 156, which surround the feedthrough wires 104. As seen in the figure, the non-conductive epoxy 150ID in the counter bore 162 of the insulator completely isolates the gold braze 115ID adhered to the wires 104 within the insulator 118. In this way, the EMI filter 158 is not in electrical contact with the gold braze 115ID. Instead, the EMI filter 158 is in electrical contact with the feedthrough wires 104 through the conductive silver epoxy 152, as shown in FIG. 8. Similarly, the EMI filter 158 is grounded to the face 111 of the flange 110 using the conductive silver epoxy 152 and, in certain instances, the additional conductive silver epoxy 168 applied at the outer joint between the EMI filter 158 and the flange 110.

Upon coupling of the EMI filter 158 with the flange 110, the filtered feedthrough assembly 100 may be placed in a fixture, which is then placed in an oven for thermal curing. Accordingly, step 1024 of the method 1000 of FIG. 2B includes thermally curing filtered feedthrough assembly 100 with the EMI filter 158 attached to the flange 110. After curing, a top mask (e.g., single sided removable adhesive) may be applied to the EMI filter 158, at step 1026. Then, at step 1028, conductive silver epoxy 164 may be dispensed into the via holes 160 of the EMI filter 158. As best understood by FIG. 10, which is a cross-sectional view of one of the wires 104 of FIG. 9, conductive silver epoxy 164 is dispensed into the via hole 160 of the EMI filter 158.

Figure 10:
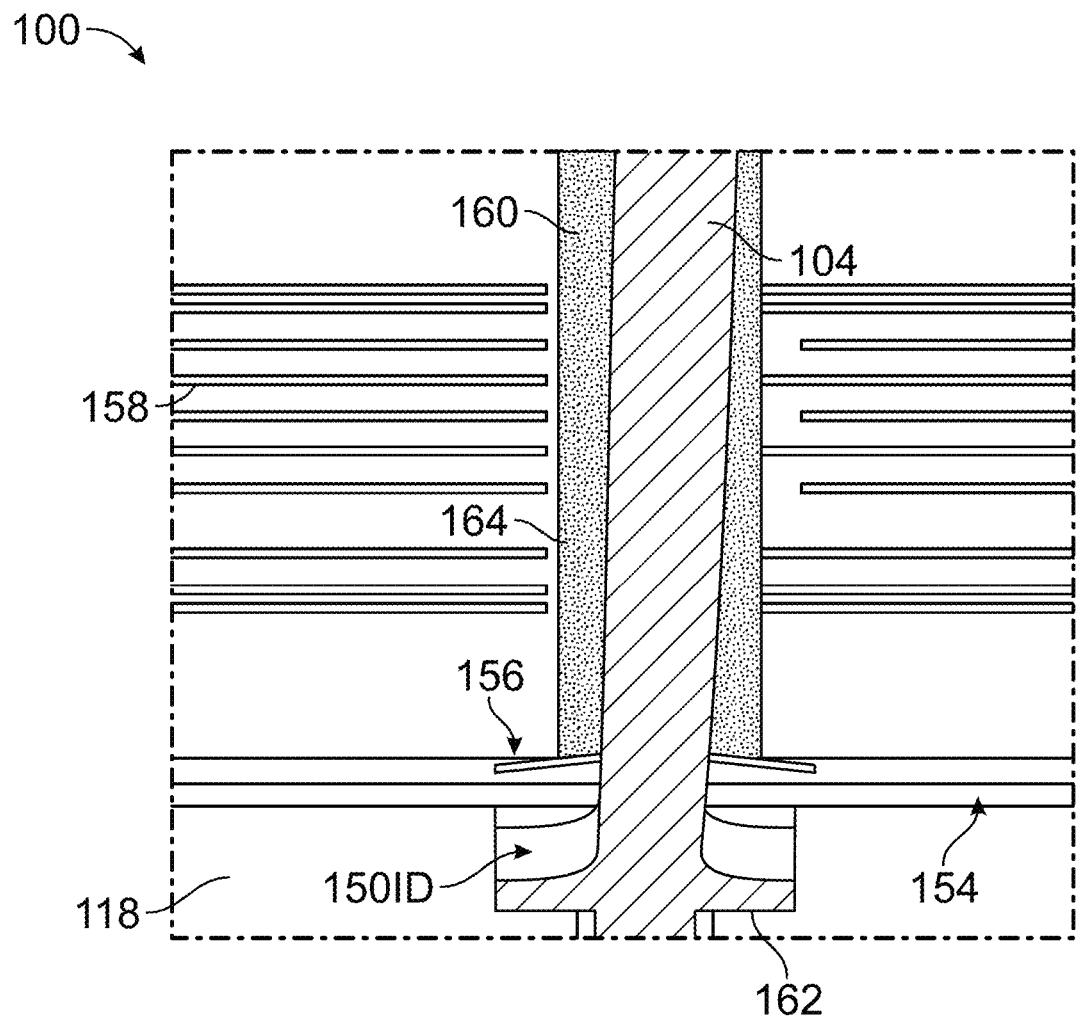
FIG. 10 is a cross-sectional side view of a single feedthrough wire extending through a portion of the EMI filter and the insulator with conductive silver epoxy dispensed into the via holes of the EMI filter.
Figure 11:
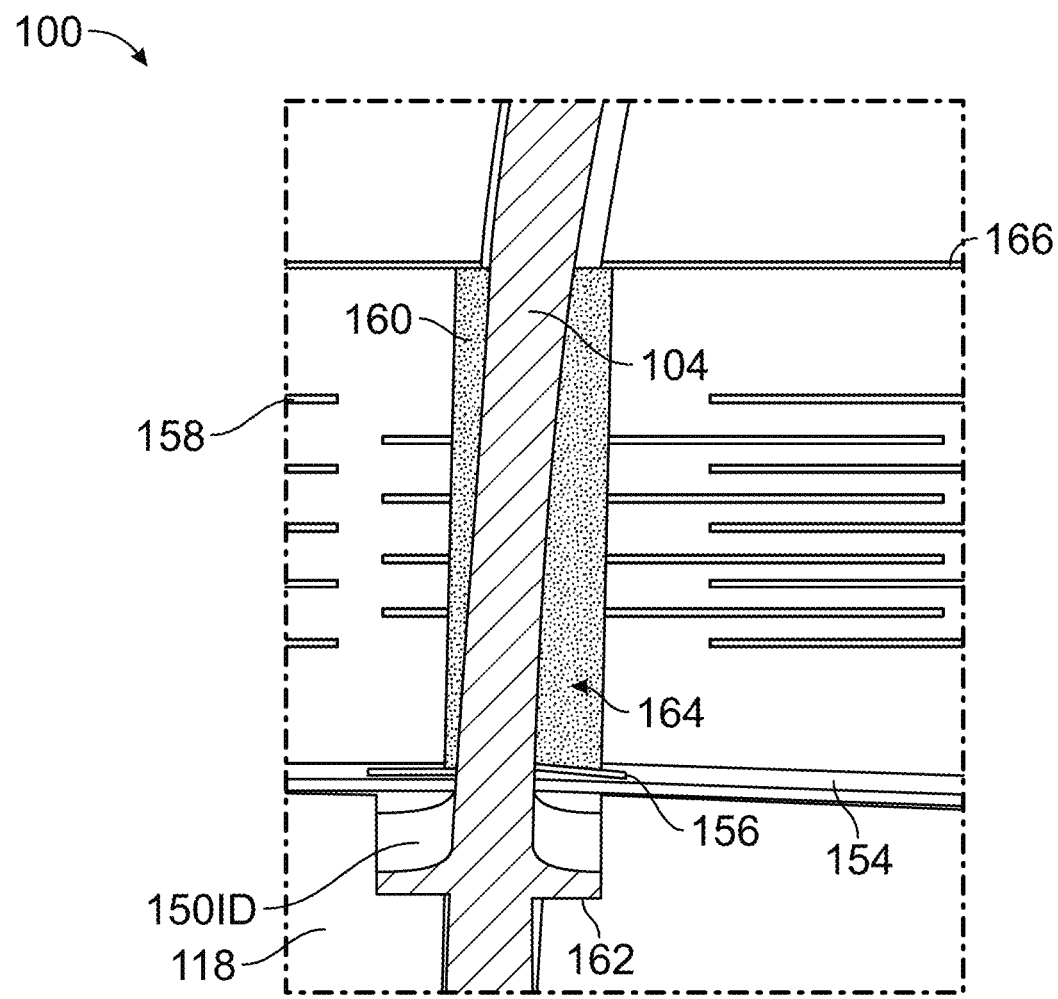
FIG. 11 is a cross-sectional side view of the assembly of FIG. 10 with the epoxy filling up the via hole and fully cured.

Once the conductive silver epoxy 164 is in the via holes 160 of the EMI filter 158, the assembly 100 may be put in a centrifuge and spun in order to allow the conductive silver epoxy 164 to settle in the via holes 160. This step 1030 is reflected in the method 1000 of FIG. 2C. The steps 1028 and 1030 may be repeated as necessary until the epoxy 164 fully fills the via holes 160 of the EMI filter 158. Once the via holes 160 are filled with epoxy 164, the epoxy 164 may be thermally cured in an oven, at step 1032 of FIG. 2C. FIG. 11, which is a cross-sectional view of the wire 104 in FIG. 10, shows the epoxy 164 fully filled in the via holes 160 of the EMI filter 158, and fully cured.

Figure 2C:
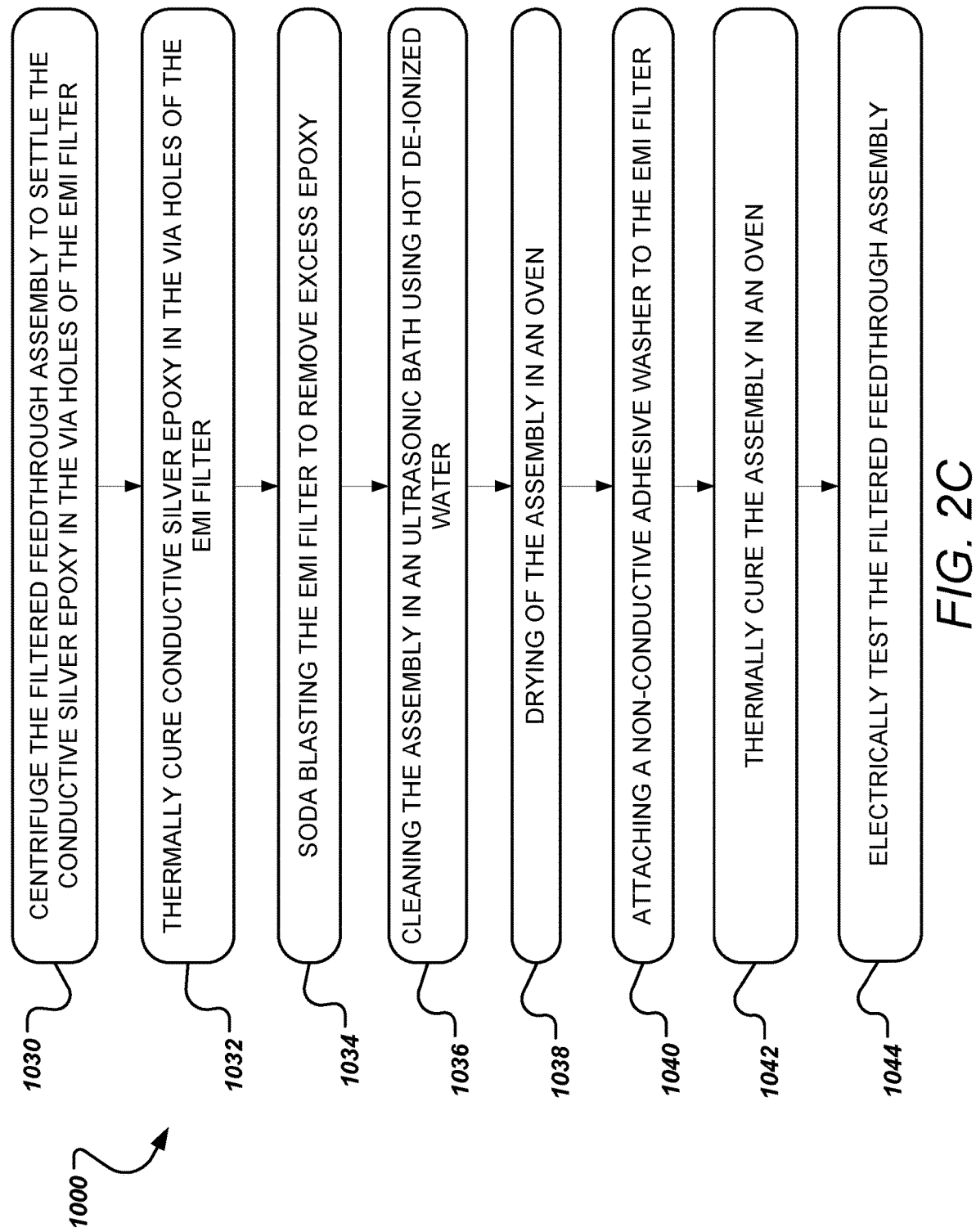

The top surface of the EMI filter 158 may be cleaned using a blasting medium (e.g., soda blasting) to remove any excess cured conductive silver epoxy 164, as seen in step 1034 of FIG. 2C. Next, the filtered feedthrough assembly 100 may be cleaned in an ultrasonic bath using hot de-ionized water, as seen in step 1036 of FIG. 2C. After the bath, the assembly 100 may be dried in an oven, as seen in step 1038 of FIG. 2C. Next, a top non-conductive adhesive washer (e.g., single sided adhesive) 166, as seen in FIG. 11, may be attached to the EMI filter 158, as seen in step 1040 of FIG. 2C. The entire assembly 100 may then be cured in the oven, as seen in step 1042 of FIG. 2C. And, once curing is complete, the filtered feedthrough assembly 100 may be electrically tested, at step 1044 of FIG. 2C. As an alternative to applying the non-conductive adhesive washer 166, a non-conductive material may be dispensed and coated to the top surface of the EMI filter 158.

FIG. 12 is a cross-sectional side view of a filtered feedthrough assembly 100 taken along the section line from FIG. 8. The only difference is that the assembly 100 in FIG. 12 is fully assembled, having completed all the steps of the method 1000 of FIGS. 2A-2C. As seen in FIG. 12, the filtered feedthrough assembly 100 has a header side 170 and a can side 172. The feedthrough wires 104 (only a single wire is seen in this cross-sectional view) extend fully through the assembly 100 to connect the electrical components of the can with the lead blocks or other components disposed within the header. Starting at the can side 172, the non-conductive adhesive 166 is adhered to the top of the EMI filter 158. The EMI filter 158 has a plurality of via holes or feedthrough ports 160. The via holes 160 are filled with conductive silver epoxy 164 so as to be electrically conductive with the EMI filter 158 and the wire 104.

At the bottom of the EMI filter 158, a washer 156 (e.g., a Kapton® washer) surrounds the wire 104. The bottom of the EMI filter 158 is adhered to a non-conductive adhesive washer 154. To the sides of the adhesive washer 154 is the UV curable epoxy 150OD that insulates the gold braze joint 115OD from contact with the EMI filter 158. The UV curable epoxy 150OD surrounds the insulator 118 above the gold braze joint 115OD. Additional UV curable epoxy 150ID is dispensed in the counter bore 162 of the insulator 118 so as to partially fill up the counter bore 162 and seal against the wire 104. The epoxy 150ID insulates the components from the gold braze joint 115ID in the through-hole of the insulator 118.

Still referring to FIG. 12, the conductive silver epoxies 152, 168 electrically connect the EMI filter 158 and the face 111 of the flange 110. This electrical connection serves as a ground path for the EMI filter 158. In this way, the potentially variable grounding path from the EMI filter 158 through the braze joints 115ID, 115OD is avoided by insulating all such areas with non-conductive epoxy 150ID, 150OD.

The foregoing merely illustrates principles of the present disclosure. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the disclosure and are thus within the spirit and scope of the present disclosure. From the above description and drawings, it will be understood by those of ordinary skill in the art that the particular embodiments shown and described are for purposes of illustrations only and are not intended to limit the scope of the present disclosure. References to details of particular embodiments are not intended to limit the scope of the disclosure.

What is claimed is:

1. A method of manufacturing a filtered feedthrough assembly for use with an implantable medical device, the method comprising:
   securing an insulator to an inner surface of a feedthrough port of a flange at a first joint;
   securing a plurality of feedthrough wires to the insulator at second joints, the second joints spaced apart from and surrounded by the first joint;
   applying a non-conductive epoxy to cover the first joint and to separately cover each of the second joints;
   applying a non-conductive washer on a face of the insulator;
   applying an electrically conductive epoxy on a can side face of the flange; and
   subsequent to applying the electrically conductive epoxy on the can side face, attaching an EMI filter to the flange via the electrically conductive epoxy so that the electrically conductive epoxy is compressed between the can side face of the flange and an opposing surface of the EMI filter to ground the EMI filter to the flange.

2. The method of claim 1, further comprising positioning disc-shaped washers on the non-conductive washer prior to attaching the EMI filter to the flange, wherein each of the disc-shaped washers surrounds a different corresponding one of the feedthrough wires.

3. The method of claim 1, wherein the EMI filter defines a plurality of capacitor ports and attaching the EMI filter to the flange comprises receiving the plurality of feedthrough wires within the capacitor ports and moving the EMI filter towards the can side face of the flange to cause the opposing surface of the EMI filter to compress the electrically conductive epoxy on the can side face.

4. The method of claim 1, wherein securing the insulator to the inner surface of the feedthrough port comprises one of brazing, soldering, or welding the insulator to the flange to form the first joint.

5. The method of claim 1, further comprising grit blasting the can side face of the flange prior to applying the electrically conductive epoxy.

6. The method of claim 1, wherein the non-conductive washer is an adhesive film and a shape of the adhesive film substantially matches a shape of the face of the insulator onto which the adhesive film is applied.

7. The method of claim 1, wherein applying the non-conductive epoxy to cover the first joint comprises applying the non-conductive epoxy in a bead that continuously extends around a perimeter of the insulator along the first joint.

8. The method of claim 7, wherein applying the non-conductive washer comprises affixing the non-conductive washer on the face of the insulator such that the non-conductive washer is surrounded by the bead of the non-conductive epoxy at the first joint.

9. The method of claim 1, wherein the insulator defines a plurality of insulator ports therethrough, and securing the plurality of feedthrough wires to the insulator at the second joints comprises inserting the feedthrough wires through different corresponding ones of the insulator ports and one or more of brazing, soldering, or welding the feedthrough wires to the insulator.

10. The method of claim 9, wherein each of the plurality of insulator ports includes a counter bore, and wherein applying the non-conductive epoxy to cover the second joints comprises dispensing the non-conductive epoxy into the counter bores while the feedthrough wires are disposed within the insulator ports.

11. The method of claim 1, wherein the non-conductive washer defines a plurality of through-holes that are sized, shaped, and positioned to each receive a corresponding one of the feedthrough wires therethrough.

12. The method of claim 1, wherein the non-conductive washer is applied on the face of the insulator such that an entirety of the non-conductive washer is surrounded by the non-conductive epoxy that covers the first joint extending around a perimeter of the insulator.

13. The method of claim 1, wherein the non-conductive washer is applied on the face of the insulator such that the non-conductive washer at least partially covers the non-conductive epoxy located at the second joints.

14. The method of claim 1, wherein the non-conductive washer is an adhesive film and is applied on the face of the insulator such that the adhesive film covers a majority of the surface area of the face of the insulator.

15. The method of claim 1, wherein the insulator is secured to an inner surface of the feedthrough port of the flange via a metallic material to form the first joint, and the non-conductive epoxy is applied to cover the metallic material at the first joint, wherein the electrically conductive epoxy is applied on the can side face of the flange at one or more locations spaced apart from the metallic material that forms the first joint.

16. A filtered feedthrough assembly for an implantable medical device, the filtered feedthrough assembly comprising:

a flange composed of an electrically conductive material and defining a feedthrough port therethrough, the feedthrough port extending from a can side face of the flange;

an insulator disposed within the feedthrough port and secured to an inner surface of the feedthrough port via a metallic material to form a first joint;

a plurality of feedthrough wires extending through the insulator and secured to the insulator at second joints which are spaced apart from, and surrounded by, the first joint;

a non-conductive epoxy that covers the first joint and separately covers each of the second joints;

a non-conductive washer disposed on a face of the insulator;

an electrically conductive epoxy disposed on the can side face of the flange and spaced apart from the metallic material that forms the first joint; and an EMI filter secured to the flange via the electrically conductive epoxy, wherein the electrically conductive epoxy is sandwiched between the can side face of the flange and an opposing surface of the EMI filter to ground the EMI filter to the flange.

17. The filtered feedthrough assembly of claim 16, wherein the non-conductive washer is an adhesive film and covers a majority of the surface area of the face of the insulator.

18. The filtered feedthrough assembly of claim 16, wherein the non-conductive washer has an oblong shape and defines a plurality of through-holes that are sized, shaped, and positioned to each receive a corresponding one of the feedthrough wires therethrough.

19. The filtered feedthrough assembly of claim 16, wherein the insulator defines a plurality of insulator ports to receive the feedthrough wires therein, each of the insulator ports including a counter bore extending from the face of the insulator, wherein the non-conductive epoxy that covers the second joints is disposed within the counter bores of the insulator port and the non-conductive washer at least partially covers the non-conductive epoxy within the counter bores.

20. The filtered feedthrough assembly of claim 16, wherein the non-conductive epoxy is in the shape of a bead that continuously extends around a perimeter of the insulator along the first joint to cover the first joint, and the non-conductive washer is surrounded by the bead.

* * * * *